US009107524B2

(12) United States Patent
Leffler

(10) Patent No.: US 9,107,524 B2
(45) Date of Patent: Aug. 18, 2015

(54) SPOON DELIVERY DEVICE

(71) Applicant: Adam Leffler, Salt Lake City, UT (US)

(72) Inventor: Adam Leffler, Salt Lake City, UT (US)

(*) Notice: Subject to any disclaimer, the term of this patent is extended or adjusted under 35 U.S.C. 154(b) by 0 days.

(21) Appl. No.: 14/254,524

(22) Filed: Apr. 16, 2014

(65) Prior Publication Data

US 2014/0223747 A1 Aug. 14, 2014

Related U.S. Application Data

(62) Division of application No. 13/220,414, filed on Aug. 29, 2011, now Pat. No. 8,898,912.

(51) Int. Cl.

| | |
|---|---|
| ***A47G 21/00*** | (2006.01) |
| ***A61J 7/00*** | (2006.01) |
| ***A01H 5/02*** | (2006.01) |

(52) U.S. Cl.

CPC ................ *A47G 21/004* (2013.01); *A01H 5/02* (2013.01); *A61J 7/0023* (2013.01)

(58) Field of Classification Search

CPC ............. A61J 7/00; A61J 7/0023; A61J 1/00; A61J 1/03; A47G 21/04; A47G 21/004

USPC ................ 30/147–150, 324–328, 123, 123.3; D7/643, 653

See application file for complete search history.

(56) References Cited

U.S. PATENT DOCUMENTS

| | | | | | |
|---|---|---|---|---|---|
| 620,792 | A | * | 3/1899 | Middleton | 30/326 |
| 784,399 | A | * | 3/1905 | Hohein | 30/326 |
| 1,390,475 | A | * | 9/1921 | Toler | 30/326 |
| 1,474,443 | A | * | 11/1923 | Rhyne | 30/326 |
| 1,708,456 | A | * | 4/1929 | Tunick | 30/326 |
| 2,072,777 | A | * | 3/1937 | Takahashi | 30/123 |
| RE21,338 | E | * | 1/1940 | Haut | 206/0.5 |
| 2,313,977 | A | * | 3/1943 | Takach | 30/326 |
| 2,877,547 | A | * | 3/1959 | Feaster | 30/322 |
| 3,054,184 | A | * | 9/1962 | Wyner et al. | 30/326 |
| 3,154,418 | A | * | 10/1964 | Lovell et al. | 30/326 |
| D204,616 | S | * | 5/1966 | Kellerman | 30/326 |
| 3,287,806 | A | * | 11/1966 | Kellerman | 30/326 |
| 3,360,121 | A | * | 12/1967 | Zoeller et al. | 30/326 |
| 3,428,460 | A | * | 2/1969 | Ely | 426/86 |
| 3,618,751 | A | * | 11/1971 | Rich | 30/326 |
| 3,662,463 | A | * | 5/1972 | Ushkow et al. | 30/326 |
| 3,664,020 | A | * | 5/1972 | Hammond et al. | 30/142 |
| 3,911,578 | A | * | 10/1975 | Ushkow et al. | 30/326 |
| 4,159,182 | A | * | 6/1979 | Adolfson | 30/324 |
| D254,229 | S | * | 2/1980 | Julius | D7/643 |
| 5,203,459 | A | * | 4/1993 | Wade | 30/326 |
| D367,804 | S | * | 3/1996 | Pierret et al. | D7/643 |
| 5,975,305 | A | * | 11/1999 | Barger | 30/326 |

(Continued)

FOREIGN PATENT DOCUMENTS

| | | | | |
|---|---|---|---|---|
| CH | 704263 | A1 | * | 6/2012 |
| DE | 102005028618 | A1 | * | 12/2006 |

(Continued)

*Primary Examiner* — Jason Daniel Prone

(74) *Attorney, Agent, or Firm* — Michael F. Krieger; Kirton McConkie

(57) ABSTRACT

A device comprising a handle and a bowl shaped so the bowl fits easily into the mouth of a patient. The bowl has prepackaged within a mixture of a gelatin or natural food such as applesauce or pudding and in some embodiments having a medicament mixed with the carrier medium in a medically efficient amount.

17 Claims, 17 Drawing Sheets

(56) References Cited

U.S. PATENT DOCUMENTS

| | | | | |
|---|---|---|---|---|
| 6,295,735 | B1 * | 10/2001 | Barger | 30/123.3 |
| 6,408,521 | B1 * | 6/2002 | Pye et al. | 30/324 |
| 6,595,110 | B1 * | 7/2003 | Huang | 30/326 |
| 6,662,454 | B2 * | 12/2003 | Harrold | 30/326 |
| 6,928,870 | B1 * | 8/2005 | Liebowitz | D10/46.2 |
| D560,442 | S * | 1/2008 | Teys et al. | D7/653 |
| D644,071 | S * | 8/2011 | Vanguard | D7/643 |
| 8,453,592 | B2 * | 6/2013 | Edwards et al. | 30/326 |
| 8,898,912 | B2 * | 12/2014 | Leffler | 30/326 |
| 2001/0045374 | A1 * | 11/2001 | Selker | 206/542 |
| 2008/0163498 | A1 * | 7/2008 | Masheah et al. | 30/326 |
| 2008/0299199 | A1 * | 12/2008 | Bar-Shalom et al. | 424/400 |
| 2009/0294454 | A1 * | 12/2009 | Harding | 220/574.1 |
| 2010/0107417 | A1 * | 5/2010 | Crisp | 30/324 |
| 2010/0107419 | A1 * | 5/2010 | Crisp | 30/324 |
| 2011/0113634 | A1 * | 5/2011 | Crisp | 30/123 |
| 2011/0146082 | A1 * | 6/2011 | Hassanpour et al. | 30/147 |
| 2012/0103356 | A1 * | 5/2012 | Crisp | 30/147 |
| 2012/0222311 | A1 * | 9/2012 | Wang et al. | 30/123 |
| 2013/0047446 | A1 * | 2/2013 | Leffler | 30/326 |
| 2014/0033541 | A1 * | 2/2014 | Crisp | 30/123 |
| 2014/0223747 | A1 * | 8/2014 | Leffler | 30/326 |
| 2015/0068047 | A1 * | 3/2015 | Leffler et al. | 30/324 |
| 2015/0075006 | A1 * | 3/2015 | Edry | 30/125 |

FOREIGN PATENT DOCUMENTS

| | | | |
|---|---|---|---|
| EP | 0778018 | A1 * | 6/1997 |
| EP | 2428141 | A1 * | 3/2012 |
| EP | 2109572 | B1 * | 8/2012 |
| FR | 2697331 | A1 * | 4/1994 |
| GB | 2373710 | A * | 10/2002 |
| NL | 1006874 | C2 * | 3/1999 |
| WO | WO 9911167 | A1 * | 3/1999 |
| WO | WO 2013039560 | A1 * | 3/2013 |
| WO | WO 2014109669 | A1 * | 7/2014 |

* cited by examiner

SPOON DELIVERY DEVICE

CROSS-REFERENCE TO RELATED APPLICATIONS

This application is a divisional of U.S. patent application Ser. No. 13/220,414 which was filed on Aug. 29, 2011 (now U.S. Pat. No. 8,898,912 B2).

BACKGROUND

1. Field of the Invention

A device comprising a handle and a bowl shaped so the bowl fits easily into the mouth of a patient. The bowl has prepackaged within a carrier medium such as a gelatin, gel, or natural food such as applesauce or pudding. Some embodiments have a medicament mixed with the carrier medium in a medically efficient amount.

2. Background and Related Art

In nursing homes, schools, prisons, hospitals, hospices and other skilled nursing facilities is often required to administer medicine to a patient who is either not able to self administer or where it would be more beneficial to assure that the medicine be administered by a caregiver. In a typical environment the caregiver verifies the temperature of the medium such as applesauce; a spoon is dipped into the applesauce and a medicine is crushed into the applesauce and then administered to the patient. Problems with this technique are that the medium such as applesauce may become adulterated or cross contaminated as several spoons are dipped into the medium. The temperature can rise over time making the medium less desirable or dangerous if left in a warm environment for too long of a period. In addition, because the medication is ground and added to the carrier, if not all of the carrier medium is consumed, than a less than medically effective amount of medicine could be administered.

BRIEF SUMMARY

The invention comprises a handle and a bowl which are designed to easily fit into the human mouth. Within the bowl is a medium such as a gel, a gelatin, a pudding, or natural foods such as applesauce. In some embodiments a medically effective amount of medicine has been premixed into the carrier medium before sealing the carrier medium in the bowl of the spoon. A protective seal than covers the top of the bowl and the entire device is pasteurized so that the device can then be packed in a sterile container and will remain sterile until administration. The spoon is constructed of food grade plastic to survive the pasteurization/sterilization process without any detrimental effects. In some embodiments, the handle is shaped with a groove so that a finger may be slid into the groove and under a portion of the film seal to assist in removal of the film seal from the top of the bowl. The top of the bowl of the spoon is designed to have smooth edges that will not damage the human mouth. The spoon can be constructed using a mold press. Once the spoons are molded from food grade plastic they are sanitized, filled with carrier medium and sealed. The entire filled and sealed spoon is then pasteurized and sterilized. They are then immediately packaged into a sanitarily lined container which is then sealed. In use, a caregiver grasps the spoon by the end of the handle and uses a second hand to slide a thumb or finger along a groove molded into the handle to assist in pulling the seal lip back away from the bowl of the spoon. Using the hand that has been holding the handle, the person can then either introduce an effective amount of medicine into the bowl or locate medicine within the handle of the device and place that into the bowl with the carrier and mix it therewith. Some embodiments have a detachable mixing extension which can be removed from the end of the spoon to mix the medicine with the carrier medium found in the bowl or the spoon. The bowl is shaped so that the final portion of the bowl which would enter a patient's mouth are shallower and tapered to fit more easily and comfortably into the human mouth.

BRIEF DESCRIPTION OF THE DRAWINGS

The objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described and explained with additional specificity and detail through the use of the accompanying drawings in which:

DETAILED DESCRIPTION

A description of embodiments of the present invention will now be given with reference to the Figures. It is expected that the present invention may take many other forms and shapes, hence the following disclosure is intended to be illustrative and not limiting, and the scope of the invention should be determined by reference to the appended claims.

Figure 1:
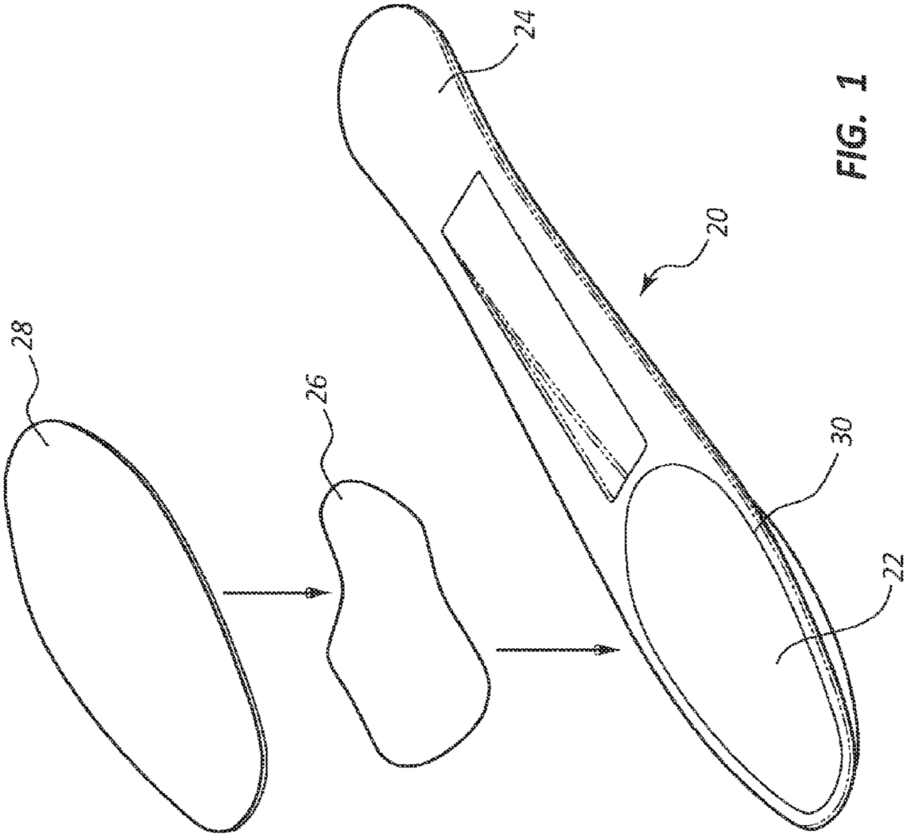
FIG. 1 shows a spoon delivery device having an indentation in the handle, a carrier medium and a seal.

Turning now to FIG. 1, a spoon-shaped medication delivery device or spoon 20 is shown having a bowl 22 and a handle 24. A carrier medium 26 can be a natural food such as applesauce or pudding or a gel or gelatin formulation. It may be desirable to create a carrier medium that is cohesive so it comes off the spoon in one piece to assure that all of the medication is consumed. Gel or gelatins may be required to avoid interaction of a natural food with the medication if stored for a long period of time. A seal 28 covers carrier medium 26 when placed into the bowl 22 and seals across a top or lip 30 of bowl 22.

Figure 2:
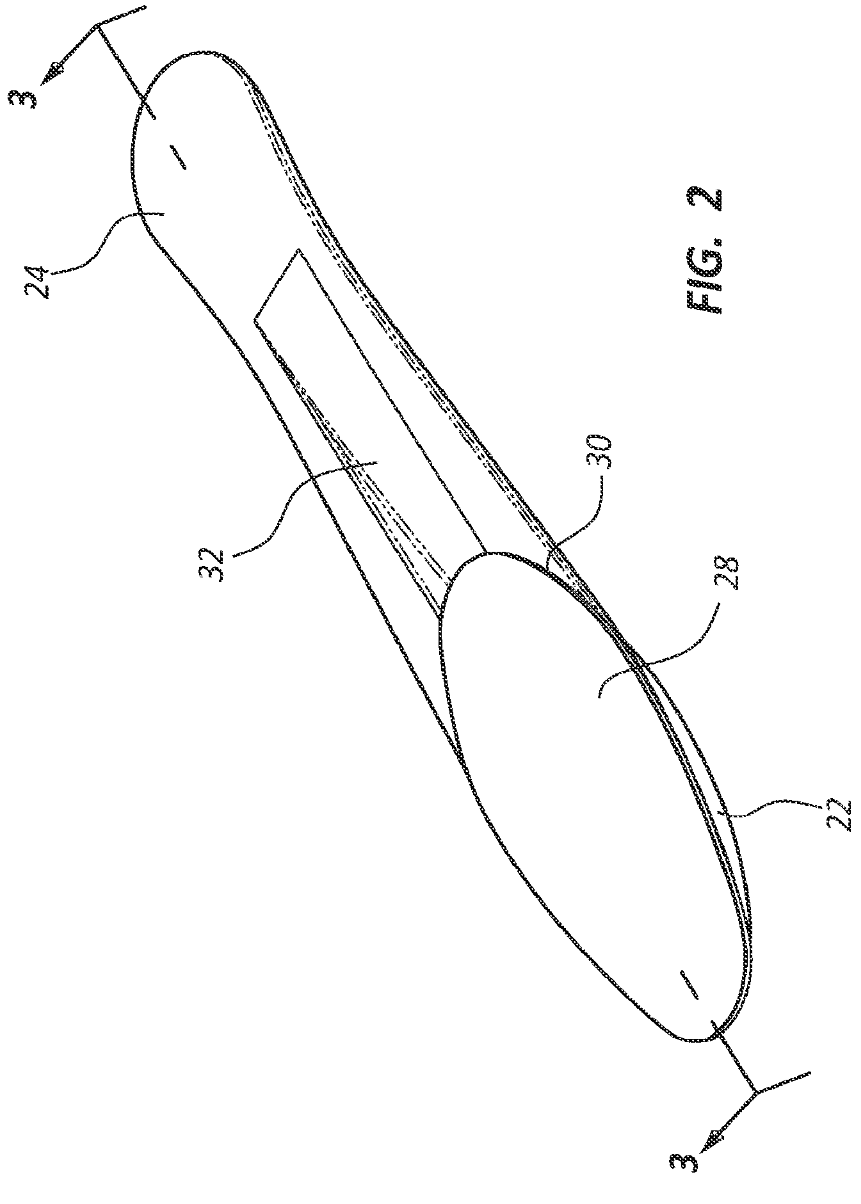
FIG. 2 shows an embodiment having a bowl in a sealed condition.

Turning now to FIG. 2, the device described in FIG. 1 is shown in its assembled condition. Seal 28 is now adhered to the top 30 of bowl 22 and covers a portion of a groove or indentation 32 formed in handle 24. Groove 32 allows a thumb or finger of a caregiver or user to be slid into the groove and under seal 28 to easily allow seal 28 to be peeled away from top 30 of bowl 22.

Figure 3:
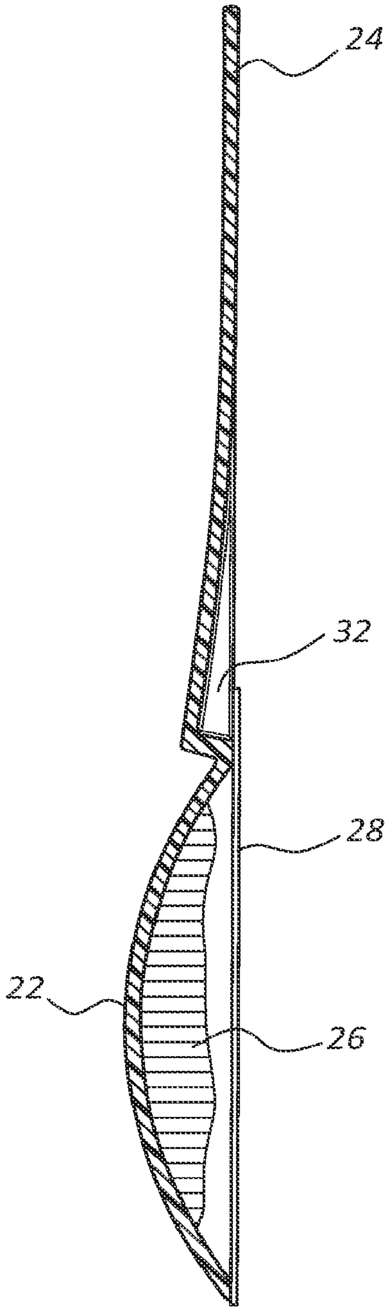
FIG. 3 is a cross sectional cut away view of the embodiment shown in FIG. 2 illustrating the seal on the bowl of the spoon with the carrier and medicine contained therein.
Figure 4:
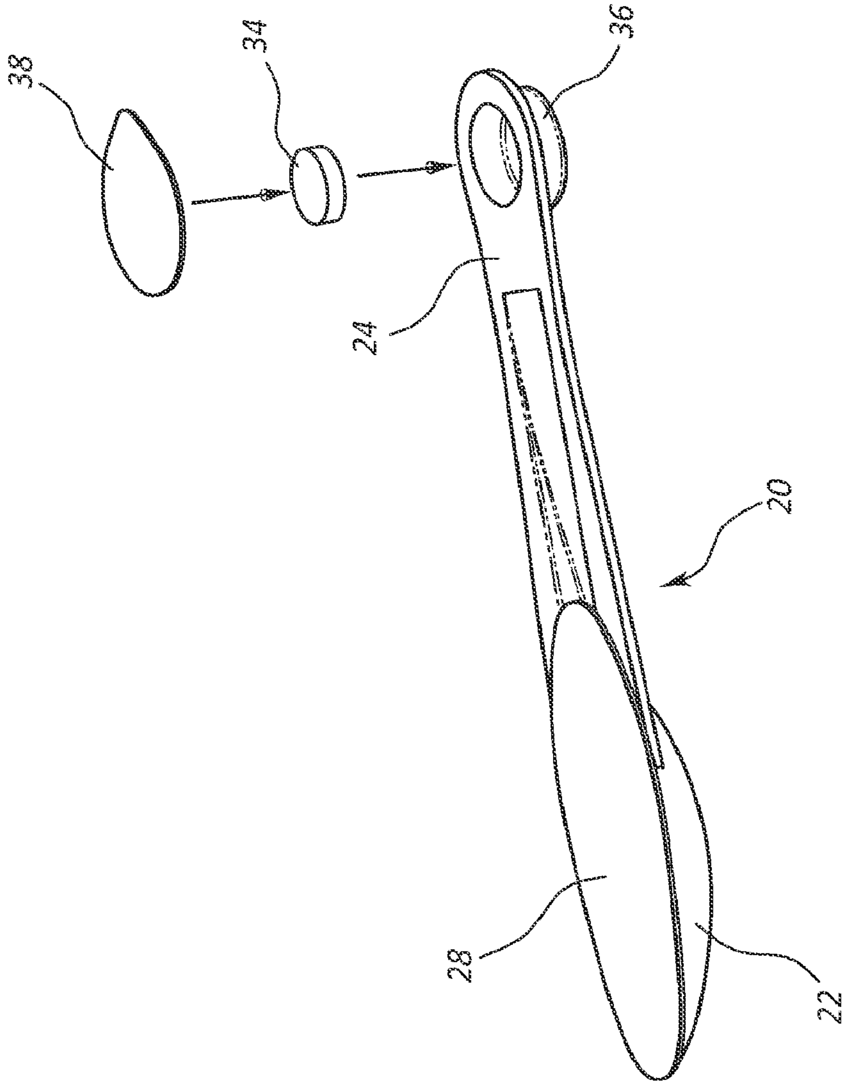
FIG. 4 is a perspective cut away view of an embodiment which contains a medication shown in a solid form which could also be a gel or a liquid stored within the handle. A medicine container in the handle of the spoon can be used so that the medicine can be kept in the handle of the spoon in cases where mixing the medicine with the carrier would shorten the shelf life or be undesirable for other reasons.
Figure 5:
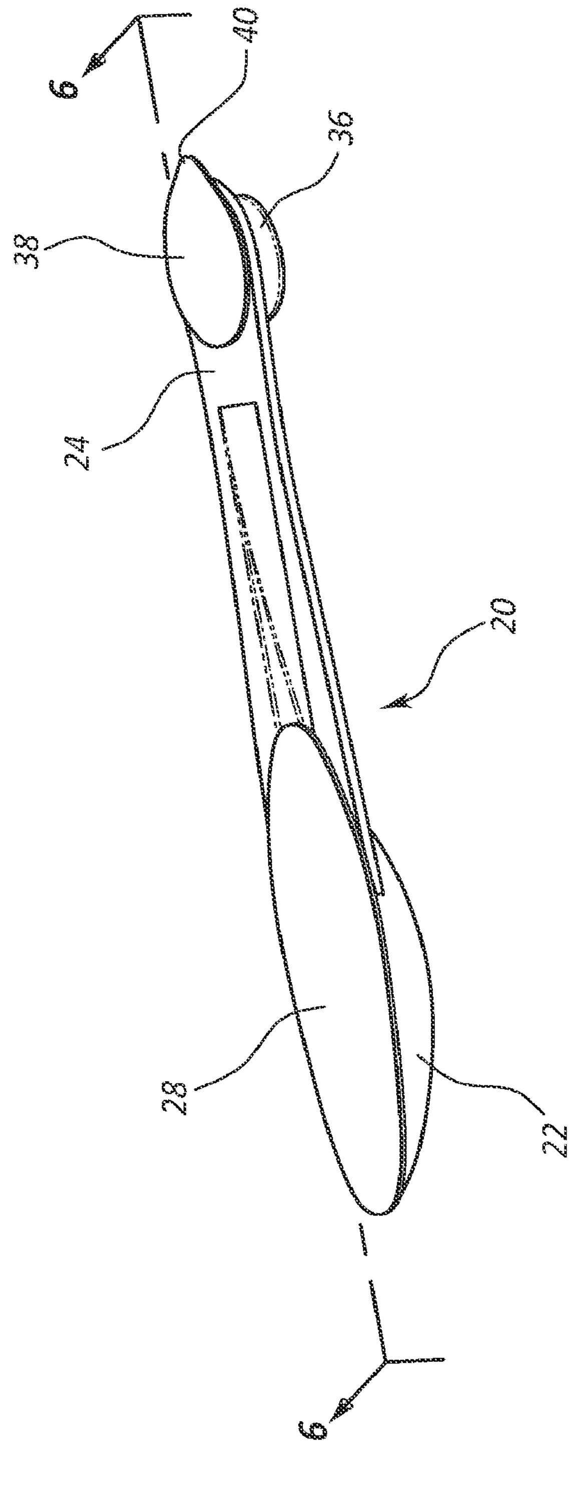
FIG. 5 shows the embodiment of FIG. 4 in a sealed condition.

FIG. 3 is a cross-sectional view of the embodiment shown in FIG. 2 showing the carrier medium 26 sealed within bowl 22 by seal 28. FIG. 4 shows an embodiment of the spoon or medicine delivery device showing a sealed bowl having only carrier medium 22. In this embodiment medicine or a medication 34 is shown stored in a well 36 formed in the handle 24. In this embodiment a well seal 38 seals medication 34 within well 36 so that the medication remains in a sterile condition. Just prior to use, in this embodiment seal 38 would be removed medication 34 would be taken out of the handle 24 and broken or ground. Seal 28 would be removed from the bowl 22 and the ground medication would be mixed with the carrier medium 26 held in the bowl 22 and then would be administered to the patient. FIG. 5 shows the embodiment shown in FIG. 4 in its assembled form having both well seal 38 and the seal over the bowl 28 affixed to the spoon 20. A tab 40 can be seen extending beyond well 36 so that the user may grasp well seal 38 and easily remove the seal when access to medication 34 is required.

Figure 6:
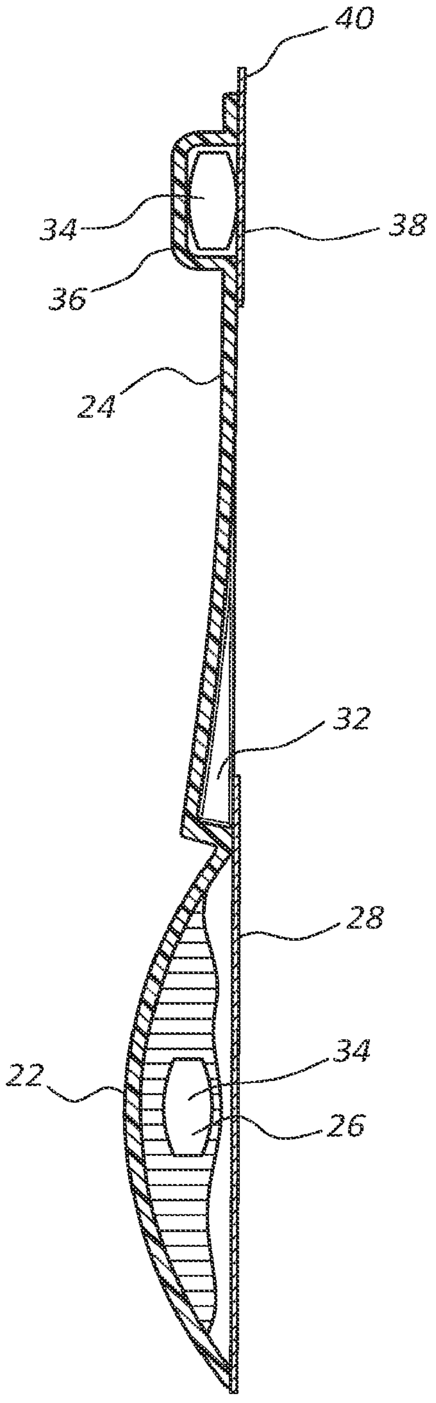
FIG. 6 shows a cross-section of the embodiment of FIG. 5 with a medicine stored both in the handle and in the bowl.
Figure 7:
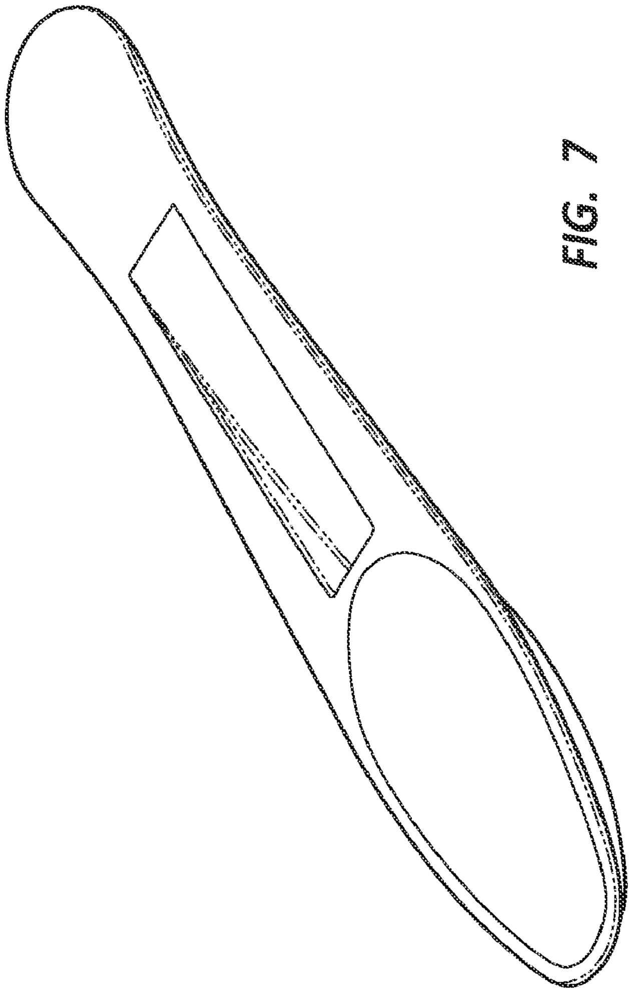
FIG. 7-12 show various embodiments of the spoon from different viewpoints.
Figure 8:
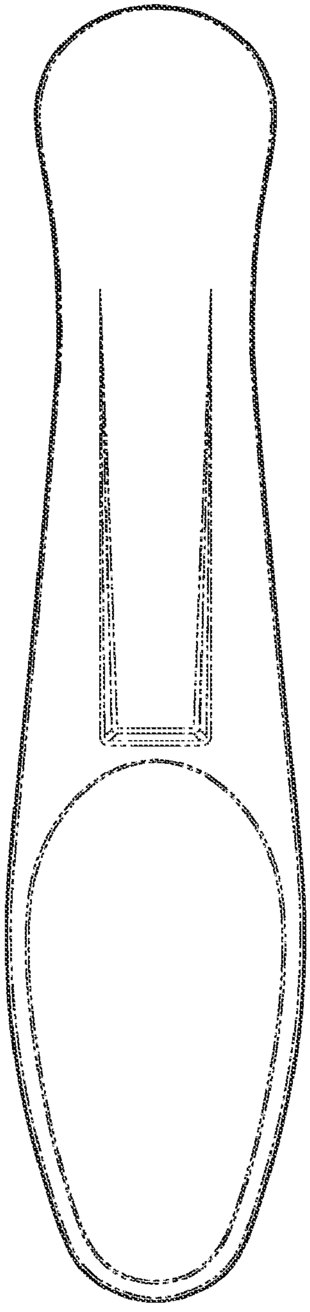
Figure 9:
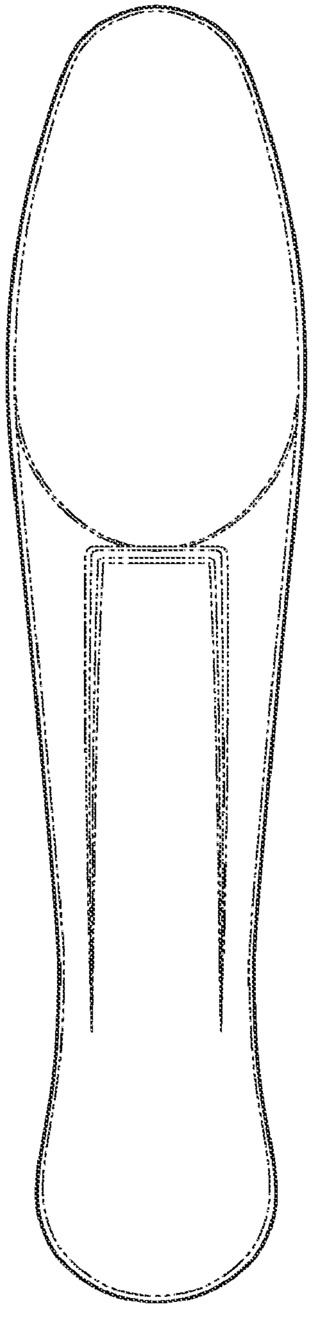
Figure 10:
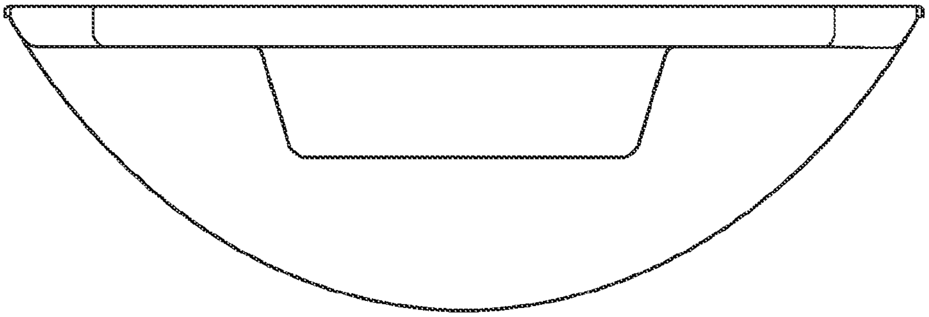
Figure 11:
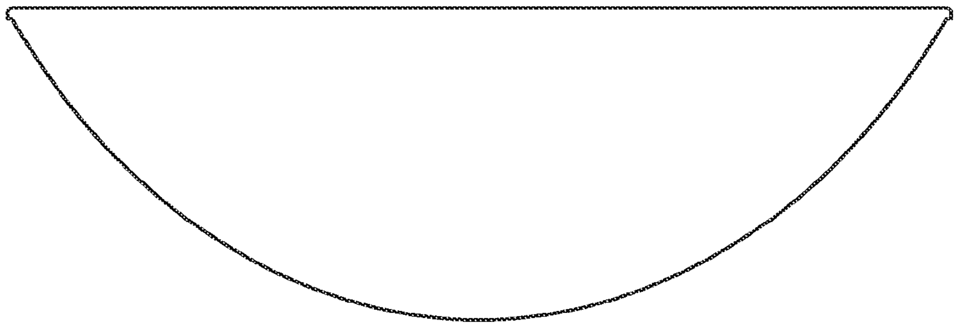
Figure 12:

FIG. 6 is a cross-sectional view of an embodiment that has a well 36 located in handle 24 and a well seal 38 within which a medication may be stored. This embodiment also has within the carrier medium 26 a separate medication which can be easily stored without degradation with the carrier medium 26. In this embodiment, two medications can be administered at the same time even though those two medications may not store well when combined. By storing one medication in well 36 and the second medication premixed with the carrier medium 26 a variety of medications can be administered at the same time which might not be able to be stored in the same location.

Figure 13:
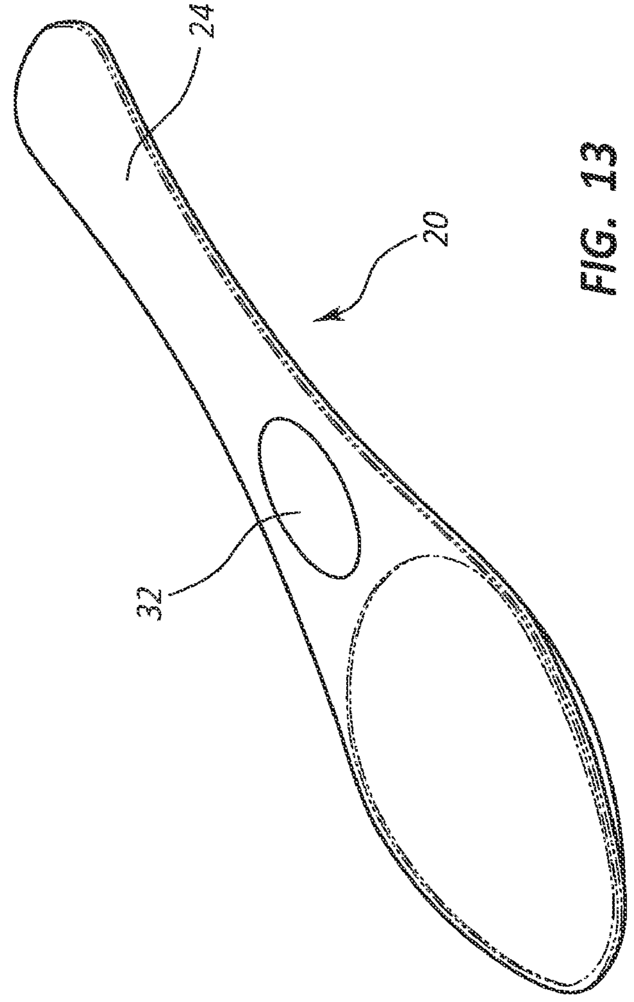
FIG. 13 shows an embodiment having an oral channel.

FIGS. 7 through 12 show an embodiment of the present invention from several viewpoints FIG. 13 shows an embodiment of the invention having a groove 32 which has a generally oval shape which may be preferable in some environments for production storage or for allowing easy release of seal 28.

Figure 14:
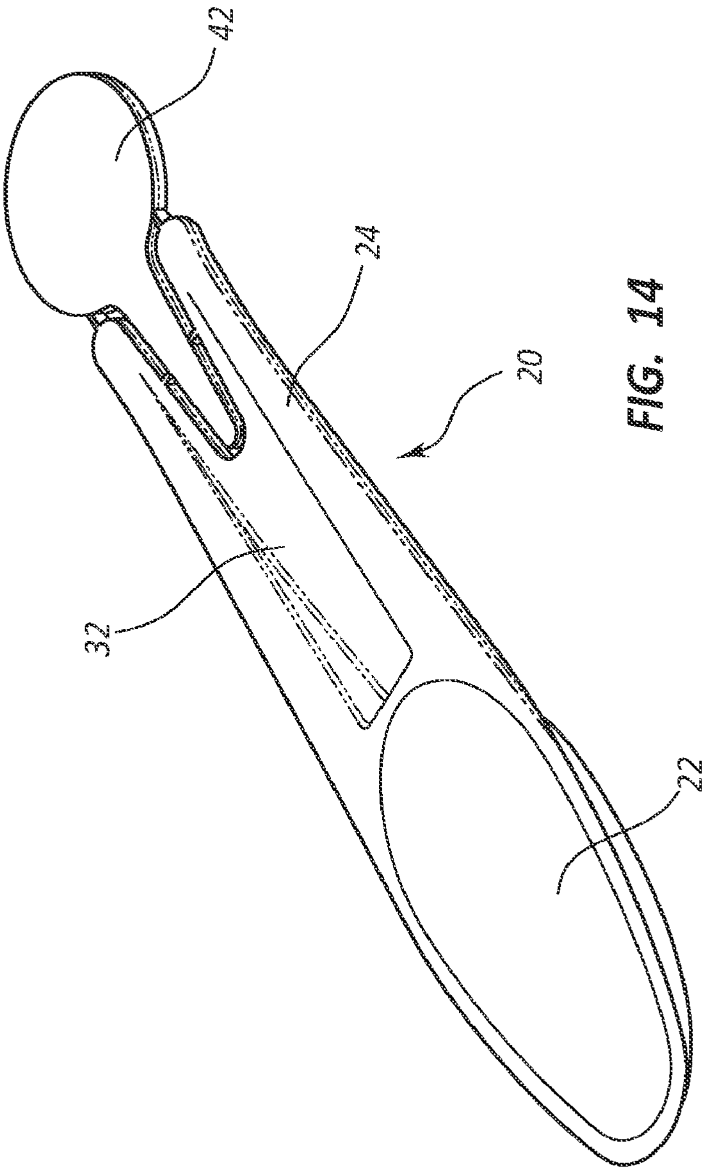
FIG. 14 shows an embodiment of the spoon having a breakaway stirring device located in the handle of the spoon.

FIG. 14 shows an embodiment having a bowl 22 and handle 24 with groove 32 but in this embodiment a mixing device 42 is attached to spoon 20.

Figure 15:
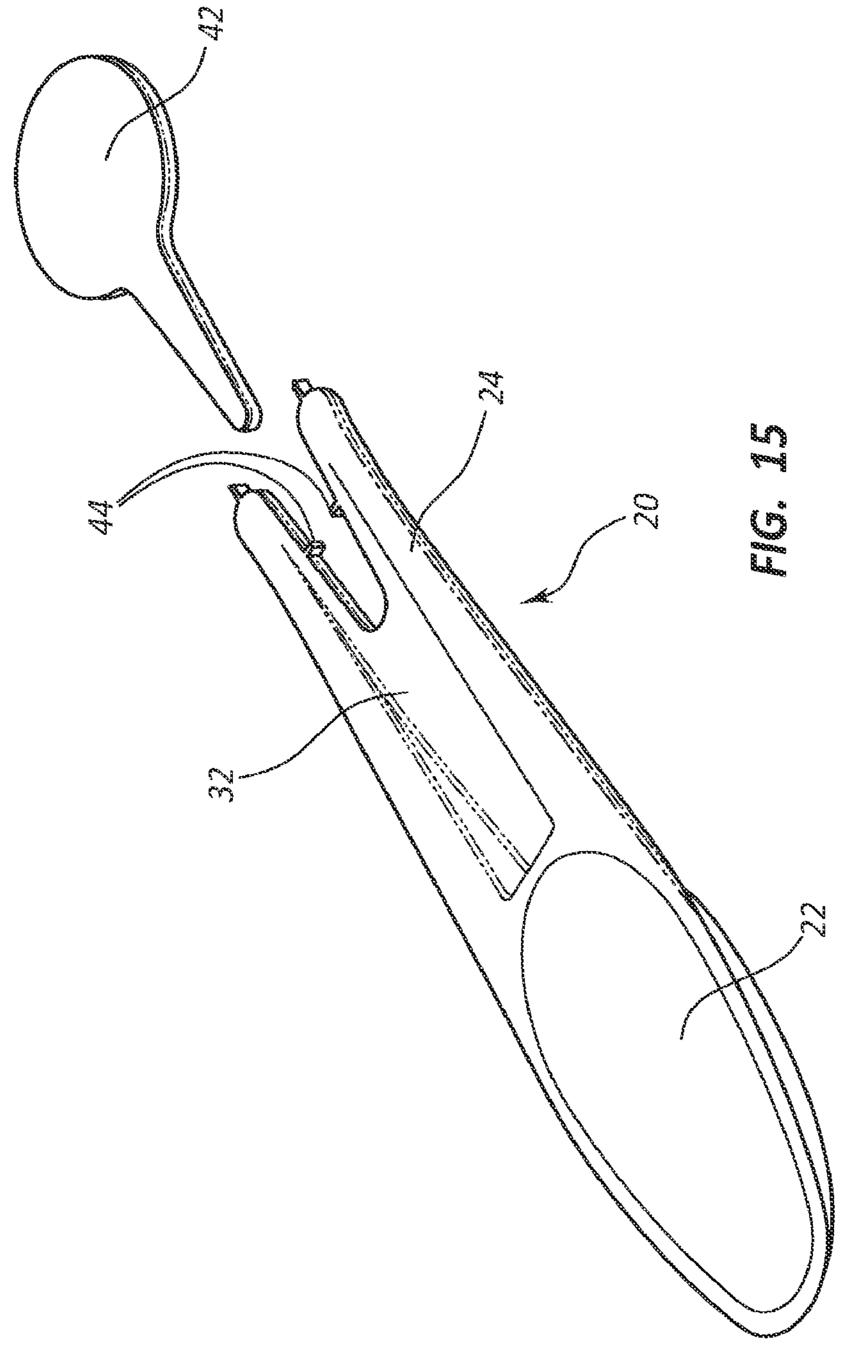
FIG. 15 shows the stirring device broken away from the handle of the spoon.

FIG. 15 shows mixing device 42 having been broken away from handle 24 where it was attached by attachment points 44. Mixing device 42 is used to combine medication with the carrier medium 26 in bowl 22 prior to administration to a patient.

Figure 16:
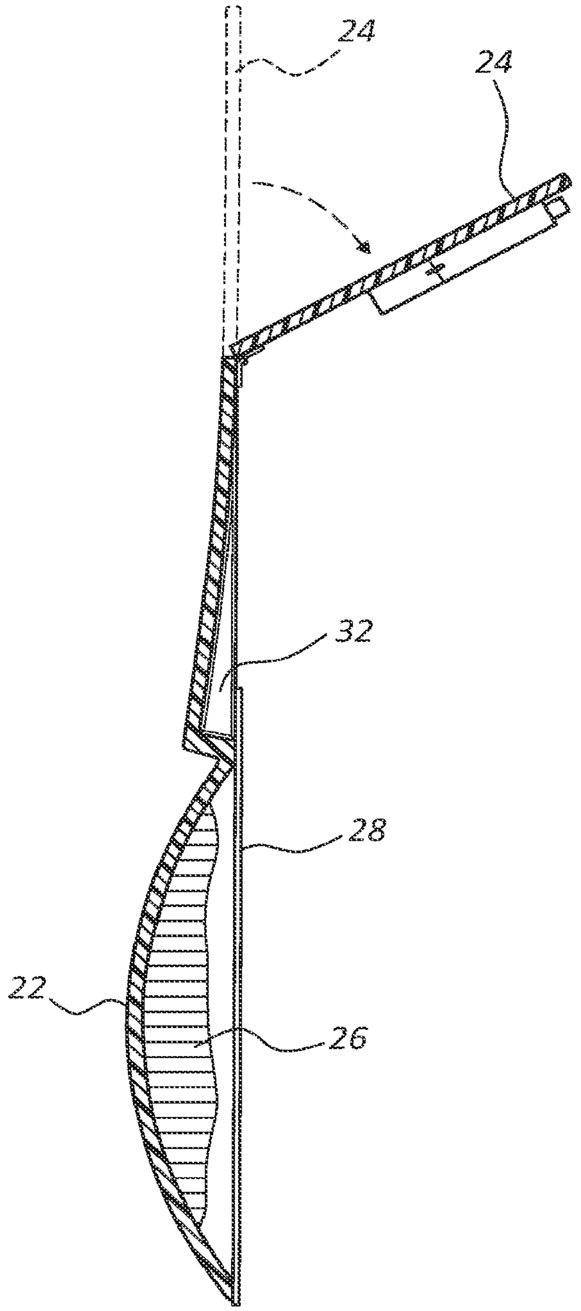
FIG. 16 shows an embodiment with a hinged handle.
Figure 17:
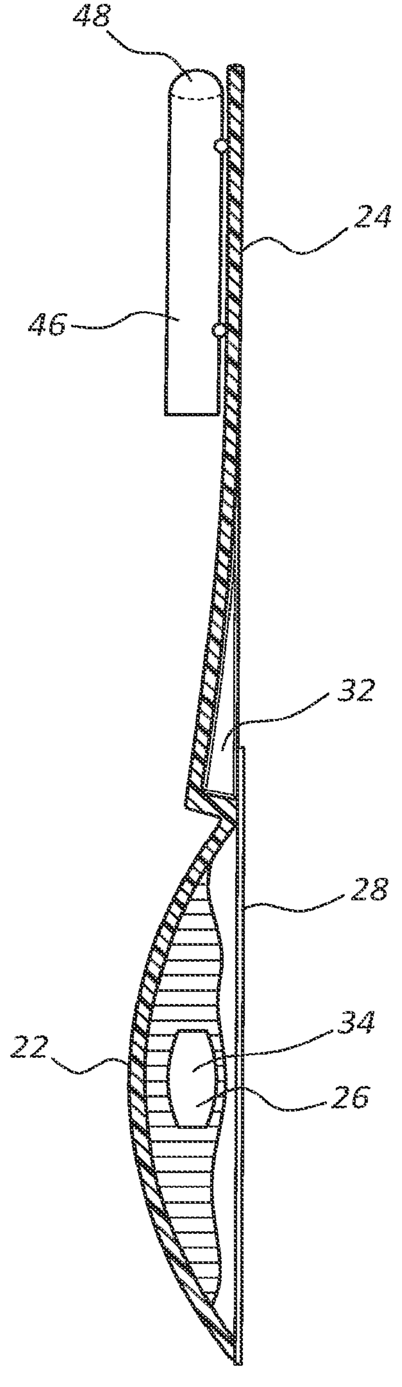
FIG. 17 depicts an embodiment wherein a squeeze tube is detachably joined to the handle.

FIG. 16 illustrates an embodiment that has a folding handle 24. FIG. 17 illustrates an embodiment that has a tube 46 formed as part of handle 24 and a cap 48 which is capable of removal allowing access to the contents of tube 46. Tube 46 may either be detachable so that the contents of the tube can be added to the carrier medium 26 in bowl 22 and then stirred and administered or in some embodiments with the folding handle 24 tube 46 is oriented so that its contents can be squirted directly into bowl 22 when in the folded position.

It will be appreciated by those skilled in the art that carrier medium 26 can be comprised of many different ingredients traditional applesauce or other food items can be sealed in bowl 22 but carrier medium 26 can also be created of artificial ingredients forming a gel that provides for a long shelf life and maybe sufficiently flavored so that the taste of some medications can be masked. Bowl 22 because of its more shallow shape allows insertion of the spoon into the mouth of patients who cannot fully open their mouth. The tapered shape of the bowl allows for insertion of the spoon between the lips and parts the lips of a patient. Additionally, handle 24 is designed with a wide surface for a firm grip by caregivers as well as allowing for groove 32 to form a channel in the handle guiding a user's thumb for easy removal of seal 28. In some embodiments, the carrier medium 26 has a slurry-like consistency and is preloaded with medication in those instances that will not deleteriously affect the shelf life. In most embodiments the slurry has no lactose or glucose and instead natural sweeteners such as stevia are used. In some of these formulas rice milk is used and in any case the ingredients must be able to undergo pasteurization without breaking down. Since the glue holding the seal 28 to the bowl 22 must also undergo pasteurization, food grade plastics and adhesives are used so that when the entire sealed spoon undergoes a 200 degree hot bath and then is quickly cooled, the entire device will be sterile and is carefully handled so that it is not contaminated as it is being packed into sterile packaging. The medically effective spoon may then be removed and administered to a patient without concern for contamination. By sterilizing each spoon and administering it to one patient, the chance of cross contamination is eliminated. The benefit of having a single serving spoon is that all of the contents are consumed by the patient and therefore all of the medication therein will be consumed. Many carrier mediums 26 because of their gel-like consistency slide out of bowl 22 in one piece and are therefore completely consumed as opposed to a more traditional medium such as applesauce wherein a patient may not consume the entire spoonful and may be require to have the spoon re-administered to completely empty the spoon.

The present invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed:

1. A medication delivery spoon for administering a medication, the spoon comprising:

a handle and a bowl at a distal end of the handle, the handle including a channel that extends towards the bowl, the handle further including an opening that extends distally from a proximal end of the handle and into the channel, the handle including a mixing device positioned within the opening;

a carrier medium contained in the bowl; and a seal over the bowl;

wherein the mixing device is removable from the handle for mixing the carrier medium contained in the bowl once the seal is removed from the bowl.

2. The spoon of claim 1, wherein the seal extends partially over the channel.

3. The spoon of claim 1, wherein the channel is ovoid.

4. The spoon of claim 1, wherein the mixing device comprises a proximal portion that extends proximally beyond a proximal end of the handle.

5. The spoon of claim 4, wherein the proximal portion is round.

6. The spoon of claim 1, wherein the channel has a depth that increases towards a distal end of the channel.

7. The spoon of claim 1, wherein the mixing device is secured to the handle by a plurality of breakable tabs.

8. A medication delivery spoon for administering a medication, the spoon comprising:

a handle and a bowl at a distal end of the handle, a proximal end of the handle including an opening that extends distally within the handle;

a carrier medium contained in the bowl;

a seal over the bowl; and a mixing device having a distal end and a proximal end, the distal end of the mixing device being positioned within the opening and being removably secured to the handle to thereby allow the mixing device to be removed from the handle and used to mix the carrier medium while the carrier medium is contained in the bowl;

wherein the handle includes a channel that extends underneath the seal, the opening extending into the channel.

9. The spoon of claim 8, wherein the carrier medium contains a medication.

10. The spoon of claim 8, wherein a portion of the mixing device extends proximally beyond a proximal end of the handle.

11. The spoon of claim 8, wherein the carrier medium comprises one of applesauce, pudding, gel, or gelatin.

12. A medication delivery spoon comprising:

a handle having a proximal end and a distal end, the handle including a channel that extends between the proximal and distal ends, the handle further including an opening that extends distally from the proximal end and into the channel;

a mixing device that is positioned at least partially within the opening of the handle;

a bowl secured to the distal end of the handle; and a seal over the bowl.

13. The medication delivery spoon of claim 12, further comprising:

a carrier medium contained within the bowl.

14. The medication delivery spoon of claim 12, wherein the seal extends partially over the channel.

15. The medication delivery spoon of claim 12, wherein the mixing device extends proximally beyond the proximal end of the handle.

16. The medication delivery spoon of claim 12, wherein the mixing device is secured within the opening via one or more breakable tabs.

17. The medication delivery spoon of claim 12, wherein the channel has a depth that increases towards the distal end of the handle.

* * * * *